United States Patent [19]

Bol et al.

[11] 4,301,790
[45] Nov. 24, 1981

[54] ENDOSCOPE WITH ELECTRIC IMAGE TRANSMISSION

[75] Inventors: Johannes Bol, Heppenheim; Meinhard Classen; Rainer Günther, both of Frankfurt; Bernhard Hugemann, Hamburg; Uwe Scheiding, Hofheim-Lorsbach, all of Fed. Rep. of Germany

[73] Assignee: Siemens Aktiengesellschaft, Berlin & Munich, Fed. Rep. of Germany

[21] Appl. No.: 57,713

[22] Filed: Jul. 16, 1979

[30] Foreign Application Priority Data

Aug. 11, 1978 [DE] Fed. Rep. of Germany ....... 2835331

[51] Int. Cl.³ .............................................. A61B 1/06
[52] U.S. Cl. .......................................... 128/6; 358/98
[58] Field of Search ......................................... 128/3–6, 128/8, 656–658, DIG. 9, 772, 786; 350/96.26; 356/241; 358/98

[56] References Cited

U.S. PATENT DOCUMENTS

| 3,375,388 | 3/1968 | Sheldon | 350/96.26 X |
| 3,452,742 | 7/1969 | Muller | 128/DIG. 9 X |
| 4,042,823 | 8/1977 | Decker et al. | 350/96.26 X |
| 4,066,071 | 1/1978 | Nagel | 128/DIG. 9 X |
| 4,074,306 | 2/1978 | Kakireuma et al. | 128/6 X |
| 4,108,211 | 8/1978 | Tanaka | 128/4X |

FOREIGN PATENT DOCUMENTS

| 526643 | 6/1931 | Fed. Rep. of Germany | 128/8 |
| 885770 | 1/1954 | Fed. Rep. of Germany | 128/6 |

*Primary Examiner*—Robert W. Michell
*Assistant Examiner*—Arthur S. Rose
*Attorney, Agent, or Firm*—Hill, Van Santen, Steadman, Chiara & Simpson

[57] ABSTRACT

In an exemplary embodiment a head with an installed television camera is present which head is connected in a plug-in fashion to a mobile tube section. The control of the orientation of the head during video exploration is effected by a system of hydraulic fluid encased Bowden cables which can transmit not only mechanical forces but also electric energizing and signal currents and which permit a conducting away of dissipated heat. The transition from the tube section to the head is sealed off by means of drawover seal.

11 Claims, 4 Drawing Figures

U.S. Patent  Nov. 24, 1981  Sheet 1 of 2  4,301,790

ENDOSCOPE WITH ELECTRIC IMAGE TRANSMISSION

BACKGROUND OF THE INVENTION

The invention relates to an endoscope with electric image transmission which consists of a head with an installed camera, a mobile tube section comprising a pivotal section and a passively flexible section, a control apparatus, and an image display device, and which is particularly suited for medical purposes.

An endoscope having electric image transmission must satisfy special requirements, particularly where it is to function for medical purposes. Above all, the head, which contains a miniaturized television camera, must be capable of being conveyed, by means of a suitable remote control, to the examination location which is usually accessible with difficulty, and said head must be pivotally adjustable to different selected orientations while at the examination location without injuring the patient. In addition, the dissipated heat, which the television camera unavoidably generates in the head, must be carried off such that excessively high temperatures do not result anywhere on the surface of the parts of the apparatus located in the patient.

In the construction of a television endoscope for e.g. stomach-intestinal-examinations, the following difficulties must be overcome:

In the head of the endoscope, a power loss of up to approximately two watts (2 W) results. However, no location of the surface of the parts of the endoscope which are disposed in the patient may exceed the body temperature by more than five kevins (5 K). In some instances, the limit of 5 K is already too high. In addition, the environment (or surroundings) of the endoscope in the patient must be essentially dry; i.e., the endoscope is not immersed in body fluid which would take up the heat and distribute it to such an extent that the mucous membranes would not be impermissibly heated. In addition, there is the fact that the patient only sometimes, not always, senses pain when he is injured by an endoscope which is too hot. Therefore, he cannot reliably warn the physician.

The head of the endoscope must manifest the shape of a circular cylinder of a maximum of approximately 15 mm diameter and a maximum of 20 mm length, and it must be capable of being slipped (or plugged) onto the tube section, it must be capable of being fully sterilized in liquids and/or gases, and it must be correspondingly sealed.

By way of summary, it is apparent that the heat discharge from the head as well as the mechanical construction of the tube section are problematic in the case of an endoscope with electric image transmission.

SUMMARY OF THE INVENTION

It has now been shown that this object can be solved in a technically very advanced manner if, in accordance with the present invention, the head is connected in a plug-in fashion to the mobile tube section of the endoscope, and if the mobility of the tube section is effected by means of a system of Bowden cables (or wires) with hydraulic fluid-filled casing and constructed so as to transmit electric current, or electric signals, respectively, as well as mechanical forces and which permits a carrying-off of the dissipated heat, the transition form the tube section to the head being sealed off by a drawover seal. Further details of the inventive endoscope are apparent from the subclaims 2 through 12.

In connection with the accompanying sheets of drawings, in schematic simplification, an embodiment of the invention is disclosed; and other objects, features and advantages will be apparent from this detailed disclosure and from the appended claims.

DETAILED DESCRIPTION

Figure 1:
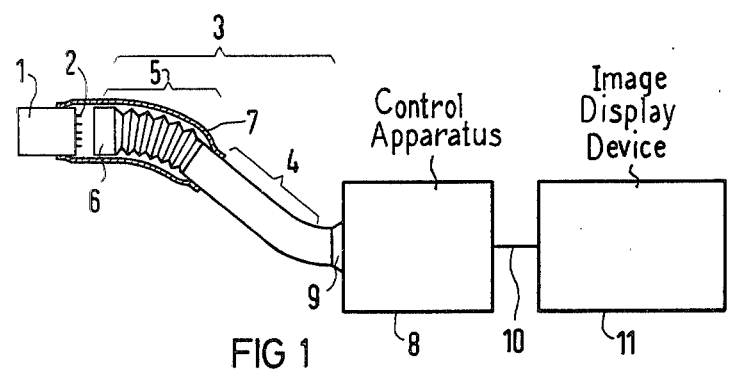
FIG. 1 illustrates the general construction of an embodiment of the television endoscope.

From FIG. 1, it is apparent head 1, designed as a separate unit, with an installed, miniaturized television camera, and with plug connector pins 2, is to be detachably connected to the socket carrier 6 of a tube section 3. The tube section 3 consists of the passively flexible section 4 and the pivot section 5 which accommodates directing of the head 1 during exploration of an interior cavity. A seal 7 for the connection of the head to the tube section is, in turn, designed as an elastic sleeve. The tube section 3 is detachably connected to the operating (or control) apparatus 8 by the coupling piece 9. An electric conduit (or cable) 0 connects the control apparatus 8 with the image display (or video) device 11, and contains the electrical conductors which connect with the respective pins 2 for effecting the camera operation and the return of the image signal.

Figure 2:
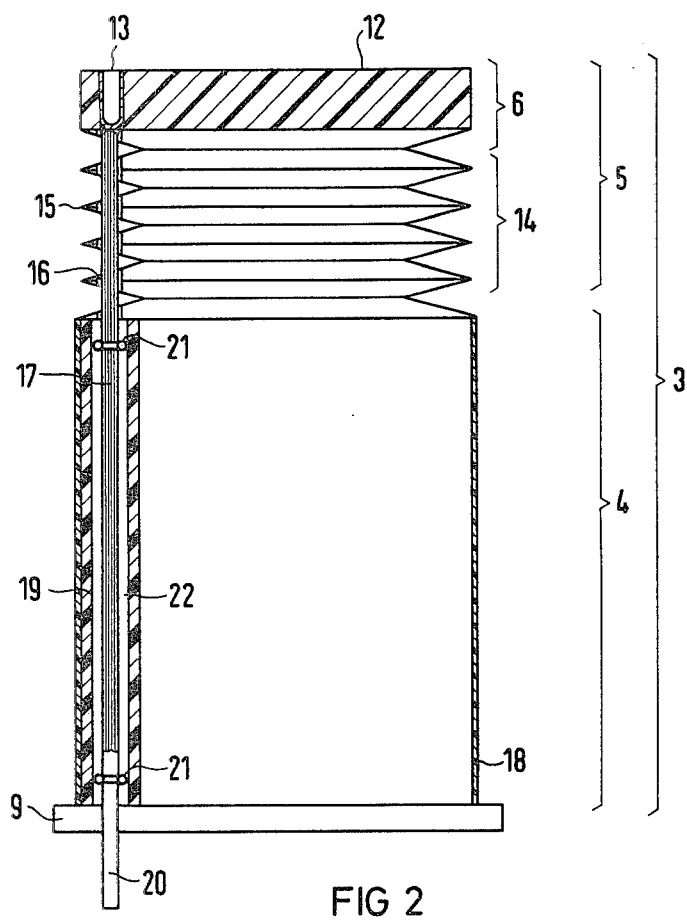
FIG. 2 illustrates the plan (or scheme) of construction of the hydraulic fluid encased actuating mechanism.

From FIG. 2, which illustrates the schematic longitudinal section through the tube section 3, it is apparent that the mobility of the carrier 6 and thus of the attached head 1 is effected by means of Bowden cables. The parts of the socket carrier 6 which are shown are its plate 12 which abuts head 1 and one of the sockets (or pin receptacles) 13. The sockets 13 and cooperating pins 2 serve the purpose of transmitting electric current or electric signals between the video camera and image display apparatus 11. The pivot section 5 of the tube section 3 has, as an external wall, a corrugated tube 14 in whose corrugations 15 at least three bores 16, which are each formed by a series of aligned apertures in corrugations 15, are provided distributed about the circumference (or periphery) of tube 3, through which push-pull cables 17 are guided. The cables 17 consist of a moderately flexible material which is nonextensible (or expandable) in the longitudinal direction; e.g. metal wire, and each cable 17 is mechanically engaged with the insulating plate 12 and connected therewith by a flexible connection. The flexible section 4 of the tube section 3 is externally sealed off with a thin-wall exterior sleeve 18, which merges into the corrugated tube in a seamless fashion. The parts 12, 14 and 18 can e.g. be fabricated from polyethylene. On the interior side of the exterior sleeve 18, flexible guide tubes 19 are attached. The guide tubes 19 can either be mounted on the interior side of the exterior sleeve 18 of the passively flexible section 4 (as shown in FIG. 2); i.e., cemented thereon, or they can be designed as channels or passages in the exterior sleeve which would then have a thicker wall while retaining its passive flexibility.

The tension or push-pull cable 17 has a somewhat lesser exterior diameter than the inner diameter of the guide tube 19. The tension cable 17 terminates in proximity to the coupling piece 9 in a rigid piston 20. The pistons 20 are individually reciprocal to direct the plate 12 and abutting head 1 during exploration. O-rings or similar sealing elements 21 are fixedly mounted on the piston 20, and on cable 17 in proximity to the corrugated tube 14, and slide in the guide tube 19. The space 22 between the sealing elements 21 and within the interior wall of the guide tube 19 and exterior to the tension cable 17 is filled with hydraulic fluid; e.g. water.

The pistons 20 penetrate the coupling piece 9 and project into the operating (or control) apparatus 8. They are moved in the control apparatus by means of a drive which is actuated from the exterior electrically or manually.

The corrugations 15 are so close together and the bores 16 have such a small diameter e.g. 10% more than the tension cable 17, that the tension cables, without the possibility of greater movement, relative to the diameter of the corrugated tube 14, are guided or constrained transversely to the longitudinal axis of the corrugated tube 14.

The described arrangement of the hydraulic Bowden cable according to FIG. 2 transfers tension and compression (push and pull) forces and movements following said forces from the piston 20 to the sockets 13.

If, relative to the cross section of the tube section 3, at least three, or better, four guide tubes 19 with pistons 20, sealing elements 21, tension cables 17, and bores 16, are installed in the tube section 3 between the socket carrier 6 with the sockets 13 and the coupling piece 9; namely, if they are distributed as uniformly as possible over the circumference of the exterior sleeve 18 of the tube section, the system allows an operator at apparatus 8 to effect desired pivoting of the socket carrier 6 in the manner required for directing the head 1 only through actuation of the pistons 20 in the coupling piece 9.

Figure 3:
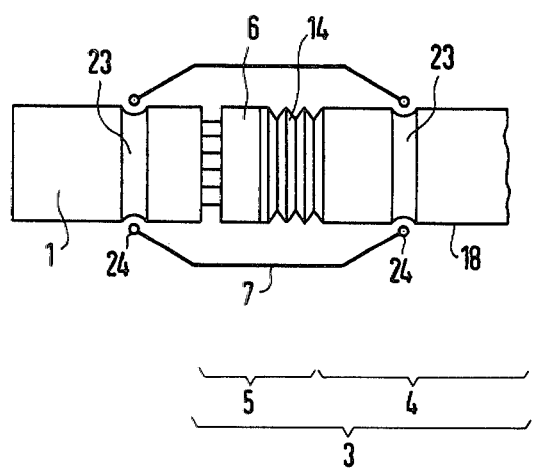
FIG. 3 illustrates an inventive embodiment of the transition from the tube to the head of the endoscope.

FIG. 3 illustrates in detail the embodiment of the sealing between head 1 and tube 3 by the seal 7.

The head 1 bears on its circumference an annular indentation (or depression) 23; tube 3 likewise bears such an annular indentation 23 on the exterior wall of its passively flexible section 4. The seal 7 is constructed in the form of an elastic sleeve, possibly with reinforced ends 24 which ends 24, in the nonstretched state, have a substantially smaller circumference than the annular indentations 23. The seal 7 between its ends is approximately equally as long as or longer than the distance between the indentations 23 in the case of a straight corrugated tube 14. In the case of a slipped-on (or plug-on) head 1, the seal 7 is drawn over the endoscope in such a manner that its ends 24 are pressed into the indentations 23 by means of their elastic force, and produce a tight seal there.

In a modified embodiment, the seal 7 is an integral component part of the exterior sleeve 18 of the hose section and, subsequent to slipping (or plugging) the head 1 on the socket carrier 6, it is drawn over the head 1 until the elastic end 24 is placed into the annular indentation 23 in the head 1.

Figure 4:
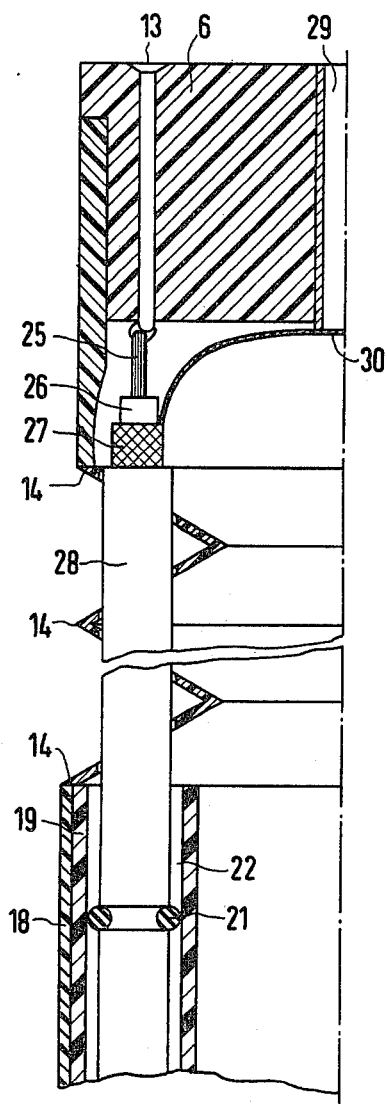
FIG. 4 illustrates the end of the tube section with plug for the head.

FIG. 4 illustrates an embodiment wherein the described mechanical actuating devices are equipped in such a manner that they additionally conduct electric current, or electric signals, respectively, to or from the plugged-on head 1 through the tube section 3, through the coupling piece 9, into the control device 8, and transport the dissipated heat away from the head 1 through the tube section 3. In the case of endoscopes for medical purposes, the heat is conducted through the exterior sleeve 18 of the tube section 3 further into the patient. The temperature of the surface of the exterior sleeve 18 of the tube section 3 is here so low that, in the case of the expected electric power losses in the head 1, internal burnings or irritations of the patient are avoided with certainty.

Compared with the above-described embodiment of the tension cables 17, coaxial cables each with an internal conductor 25, insulation 26, a flexible shield 27 for conducting electric current and heat and conventionally consisting of metal mesh, and an insulating sheathing 28, are utilized. The inner conductor 25 are electrically and mechanically connected with respective sockets 13 in the socket carrier 6 which correspond to their position. The shields 27 of the coaxial cables are in connection with respective thermal sockets 29 in the socket carrier 6 preferably by means of flexible heat conductive bridging members 30. The thermal sockets 29 assume (or take over) the dissipated heat from thermal plugs secured to the head 1 and in effective heat exchange relation with the heat dissipating components within the head 1. The sealing elements 21 are, in this instance, mounted on the sheathing 28 of the coaxial cables, and on the pistons 20, respectively. In FIG. 4, an embodiment is illustrated wherein one central thermal socket 29 is connected to the shields 27 of all coaxial cables. Otherembodiments have several thermal sockets 29 which are connected to various shields 27, respectively. The individual shields 27 with their respective thermal sockets 29 can additionally be utilized for the transport of electric current, or electric signals, respectively.

The dissipated heat of head 1 arriving from the at least one thermal socket 29 can thereby find its path from the shields 27 through the insulating sheathing 28, through the hydraulic fluid in the guide tube 19, through the wall of the guide tube 19, and/or through the exterior sleeve 18 of the tube section 3, toward the exterior. Due to the large surface of the exterior sleeve 18, the exterior temperature of the tube section 3 is thus increased so little that, in the case of endoscopes for medical purposes, the discharge (or carrying-off) of the dissipated heat to the mucous membranes of the patient and from there into his blood circulation is viable.

A carrying-off of the dissipated heat in the above-described manner is necessary since all cooling systems in which the dissipated heat of the head 1 is conveyed out of the patient by means of a flowing medium (or agent) are not usalbe on account of the lack of space in the tube and on account of the requirement (or condition) that the head 1 be connected to the tube section 3 in a plug-in fashion. This applies, in particular, to circulatory cooling systems and heat tubes.

A heat-emission directly to the patient by means of radiation, transmission through the air, or thermal conduction to the mucous membranes to be contacted for this purpose is also not possible since the above-cited limit of five kelvins (5 K) temperature difference relative to the body temperature would then be exceeded by several orders of magnitude.

In order to prevent the heat generated in head 1 from being transferred directly to the patient, in the head 1 thermally generating electronics are thermally insulated as well as possible from the exterior surface of head 1. The only connections which conduct the heat well lead into one or more pins on the head 1 which, pursuant to slipping-on (or plug-on) of the tube section 3, are plugged into the thermal sockets 29 and/or the sockets 13.

The following example shows the order of magnitude of the temperature gradations along the path of the heat:

2 W heat output (or power), maximally 20 mm length of the heat path in the head 1, several heat conductors consisting of copper of 2 mm² cross section altogether, temperature difference from the beginning of the heat conductor to its end (=end of the plug-on head 1), a maximum of 30 K.

The unfavorable instance—because it leads to particularly great temperature gradients—is assumed which is that the heat is transmitted in bundled (confined) fashion from a pin on the head to only one thermal socket 29 in the carrier 6:

Transistion area (or surface): pin-thermal socket, approximately 100 mm²; gap between pin and thermal socket, approximately 0.01 mm, to be filled with grease; 2 W heat current, approximately one kelvin (1 K) temperature difference between pin and thermal socket 29.

For the numerical example, a further embodiment of the invention is assumed. According to this embodiment, a heat distributor is installed on, or closely beneath, the surface of the exterior sleeve 18 of the tube section 3, which heat distributor consists of bands or wires. In order to not reduce the flexibility of the tube region 4 too much, the bands or wires are wound or coiled about the longitudinal axis of the hose 3 e.g. in the form of a helical configuration. However, the wires can also be constructed in the form of a mesh. The bands, or wires, respectively, consist of a material which is a good heat conductor; for example, silver, copper, or aluminum. At the head-side end of the exterior sleeve 18 of the tube section 3, the heat distributor is conveyed out from the latter and connected to the thermal socket or sockets 29.

The heat from the thermal sockets 29 spreads out in the heat distributor and egresses, in a large area, to the circulating air, or it spreads out by means of thermal conduction into the surrounding regions; for example, the mucous membranes of the patient where it is transported away by his blood circulation. The temperature of the heat distributor will correspondingly decrease from head 1 along the length of the tube 3.

If the surface temperature of the heat distributor becomes to high in proximity of the heat 1, the heat distributor can be covered there with a material which is a relatively poor heat conductor serving as a thermal resistance. The technically simplest solution is to have the heat distributor run within the exterior sleeve 18 of the tube section 3. The following example contains the figures for such an embodiment:

The coefficient of thermal conductivity of the heat distributor consisting of Cu-alloys is approximately 300 $Wm^{-1}K^{-1}$. The coefficient of thermal conductivity of the mucous membrane of the patient is approximately 0.2 $Wm^{-1}K^{-1}$. The cross section of the heat distributor is approximately 10×0.1 mm. The mean thickness of the mucous membrane is approximately 1 mm to the blood stream. The heat current is 2 W. The temperature difference between the apparatus and the blood circulation lies substantially below one kelvin (1 K) already at the head-side end of the heat distributor.

It will be apparent that many modifications and variations may be effected without departing from the scope of the novel concepts and teachings of the present invention.

We claim as our invention:

1. An endoscope with electric image transmission, comprising: a head (1) with an installed camera, a mobile tube section (3) comprising a pivotal section (5) and a passively flexible section (4), a control device (8) and an image display device (11), the head (1) being connected in a plug-in fashion in said pivotal section (5) of the mobile tube section (3), and force transmitting cables (17) mechanically coupling said pivotal section (5) with said control device (8) for controlling the mobility of the pivotal section (5) of the tube section (3) and thereby effecting pivotal movement of said head (1), and said cables (17) being formed of electrical transmission means (25-28) capable of transmitting electrical energy as well as mechanical forces, and providing electrical coupling via said electrical transmission means (25-28) between said camera and said image dislay device (11), and said cables (17) comprising heat transmission means (27, 28) in heat transfer coupling with said head (1) via said pivotal section (5) for accommodating a carrying-off of dissipated heat from said head (1) to said cables (17), and a drawover seal (7) sealing the transition from the tube section (3) to the head (1).

2. An endoscope according to claim 1, with the pivotal section (5) comprising a corrugated tube (14) having a longitudinal axis and having corrugations (15) extending about the longitudinal axis, said corrugations (15) having outermost exterior wall portions defining a maximum diameter of the corrugated tube (14) and defining a circumference of the corrguated tube (14), said corrugations (15) having at least three bores (16) which are in alignment with the respective cables and are distributed over the circumference of the corrugated tube (14), said force transmitting cables each comprising an actuating cable (17) having a given diameter, and one of the actuating cables extending through each of the bores (16) with the bores (16) having a diameter which is only slightly greater than the diameter of the actuating cables (17), and the corrugations (15) of the corrugated tube (14) being so closely disposed to each other that the actuating cables (17), relative to the maximum diameter of the corrugated tube (14), cannot execute any major movements transversely to the longitudinal axis of the corrugated tube (14).

3. An endoscope according to claim 2, with the passively flexible section (4) comprising an exterior sleeve (18), in proximity of the corrugated tube (14), and having an increased thermal resistance such that heat traveling through the tube wall forward the exterior is capable of bringing the exterior side of the exterior sleeve (18) to only a slightly increased temperature.

4. An endoscope according to claim 1, with the flexible section (4) having guide tubes (19) which provide interior passages for the cables (17), the passages in the guide tubes (19) having only a slightly greater diameter than the cables (17).

5. An endoscope according to claim 4, with the cables (17) terminating in one rigid piston (20) each, in the proximity of the control device (8), and sealing elements (21) being mounted on each piston (20) and on the cable (17), the sealing elements (21) being slidable in the guide tubes (19), and the interior passages of the guide tubes (19) providing interior spaces (22) limited by the sealing elements (21), and filled with hydraulic fluid, as a consequence of which push and pull forces and movements following said forces can be transmitted from the pistons (20) to the pivotal section (5) which is connected with the cables.

6. An endoscope according to claim 1, with the cables being constructed as coaxial cables, and comprising an inner conductor (25), insulation (26), a flexible shield (27) which conducts electric current and heat, and an insulating sheaving (28), the mobile tube section (3) having a carrier (6) with sockets (13) for plug-in reception of the head (1), the inner conductors (25) being connected with those sockets (13) which correspond with regard to their position in the carrier (6) to the position of the coaxial cables.

7. An endoscope according to claim 6, with the carrier (6) including at least one thermal socket (29), and the shield (27) of each of the coaxial cables being connected to the at least one thermal socket (29), whereby the inner conductors (25) of the coaxial cables are effective for the transport of electrical energy while the shields (27) provide for the transport of electric current and heat.

8. An endoscope according to claim 7, with thermal bridges (30) connecting the shields (27) of the coaxial cables to the at least one thermal socket (29).

9. An endoscope according to claim 7 with parts in the interior of the head (1), which generate the dissipated heat, being thermally insulated from the exterior wall of the head, and the mobile tube section (3) having means connected to the at least one thermal socket (29) which carries away the heat.

10. An endoscope according to claim 1, with the head having an external wall with an annular depression (23) therein providing a minimum circumference about the head, the passively flexible section (4) having an annular depression (23) defining a minimum circumference of the passively flexible section (4), the drawover seal (7) having the form of a sleeve having annular ends (24) each with a given circumference, and being formed of an elastic material, and the circumference of said ends (24), in the nonstretched state, being less than the circumference of said annular depressions (23), provided in the wall of the head (1) and in the passively flexible section (4), such that the ends (24) of the drawover seal (7), in the stretched state, lie fixedly in said indentations (23), whereby the pivot section (5) and the head (1) where connected with the tube section (3) is sealed off toward the exterior.

11. An endoscope according to claim 10, with the drawover seal (7) being constructed in the form of an integral component part of the passively flexible section (4) and having an elastic end (24) which, after plugging the head (1) onto the tube section (3), is drawn into the annular indentation (23) in the wall of the head (1).

* * * * *